United States Patent
Voegel et al.

(10) Patent No.: US 6,858,647 B2
(45) Date of Patent: Feb. 22, 2005

(54) RETINOID COMPOUNDS SUITED FOR ANTIBACTERIAL APPLICATIONS

(75) Inventors: Johannes Voegel, Châteauneuf/Grasse (FR); Marie-Thérèse Cavey, Peymeinade (FR)

(73) Assignee: Galderma Research & Development S.N.C., Valbonne (FR)

( * ) Notice: Subject to any disclaimer, the term of this patent is extended or adjusted under 35 U.S.C. 154(b) by 3 days.

(21) Appl. No.: 10/207,777

(22) Filed: Jul. 31, 2002

(65) Prior Publication Data

US 2003/0055110 A1 Mar. 20, 2003

Related U.S. Application Data

(63) Continuation of application No. PCT/FR01/00280, filed on Jan. 30, 2001.

(30) Foreign Application Priority Data

Jan. 31, 2000 (FR) .............................. 00 01206

(51) Int. Cl.$^7$ ............................................ A61K 31/355
(52) U.S. Cl. ...................................... 514/458; 514/859
(58) Field of Search ................................. 514/458, 859

(56) References Cited

U.S. PATENT DOCUMENTS

| | | | |
|---|---|---|---|
| 4,717,720 A | | 1/1988 | Shroot et al. |
| 4,874,747 A | | 10/1989 | Shroot et al. |
| 5,188,817 A | * | 2/1993 | Ozick .......................... 424/49 |
| 5,574,036 A | | 11/1996 | Bernardon et al. |
| 5,723,499 A | | 3/1998 | Charpentier et al. |
| 5,942,531 A | * | 8/1999 | Diaz et al. .................. 514/394 |
| 5,952,382 A | | 9/1999 | Bernardon |
| 5,998,395 A | | 12/1999 | Kligman |
| 6,017,938 A | | 1/2000 | Bershad |
| 6,150,413 A | | 11/2000 | Bernardon et al. |
| 6,248,749 B1 | | 6/2001 | Demarchez et al. |
| 6,316,009 B1 | | 11/2001 | Bernardon et al. |

| | | |
|---|---|---|
| 2002/0035161 A1 | 3/2002 | Segura et al. |

FOREIGN PATENT DOCUMENTS

| | | |
|---|---|---|
| AU | 687687 B | 2/1998 |
| AU | 753735 B2 | 10/2002 |
| EP | 0199636 A1 | 10/1986 |
| EP | 0292348 A1 | 11/1988 |
| EP | 0379367 * | 7/1990 |
| EP | 0658553 A1 | 6/1995 |
| EP | 0679631 A1 | 11/1995 |
| EP | 0740937 A2 | 11/1996 |
| EP | 0879814 A1 | 11/1998 |
| FR | 2736548 A1 | 1/1997 |
| FR | 2761600 A1 | 10/1998 |
| FR | 2767525 A1 | 2/1999 |
| FR | 2787322 A1 | 6/2000 |
| WO | 93/15740 A1 | 8/1993 |
| WO | 97/09987 A1 | 3/1997 |
| WO | 98/18440 A2 | 5/1998 |

OTHER PUBLICATIONS

Gollnick et al., "Topical Drug Treatment in Acne", *Dermatology*, XX, XX, vol. 196, No. 1, pp. 119–125 (1998), Karger, Basel, Switzerland.

Gollnick et al., "Topical Therapy in Acne", *J. Eur. Acad. Dermatol. Venereol.*, vol. 11, No. suppl. 1, pp. S8–S12 and discussion S28–S29 (1998), Elsevier Science Publishers, Amsterdam, Netherlands.

Bergfeld, "Topical Retinoids in the Treatment of Acne Vulgaris", *J. Drug Dev. Clin. Prct.*, vol. 8, No. 3, pp. 151–160 (1996), Gardiner–Caldwell Communications, Macclesfield, Chesire, United Kingdom.

* cited by examiner

*Primary Examiner*—Kevin E. Weddington
(74) *Attorney, Agent, or Firm*—Burns, Doane, Swecker & Mathis L.L.P.

(57) ABSTRACT

A variety of retinoid compounds well suited for preventively or curatively treating a bacterial colonization infesting/infecting an individual subject exhibit pronounced antibacterial activity, notably pronounced antibacterial activity in respect of the bacterium *Staphylococcus aureus*, and are also well suited for the cleansing/deodorizing of human skin.

55 Claims, No Drawings

RETINOID COMPOUNDS SUITED FOR ANTIBACTERIAL APPLICATIONS

CROSS-REFERENCE TO PRIORITY/PCT APPLICATIONS

This application claims priority under 35 U.S.C. § 119 of FR-00/01206, filed Jan. 31, 2000, and is a continuation of PCT/FR01/00280, filed Jan. 30, 2001 and designating the United States (published in the French language on Aug. 9, 2001 as WO01/56554 A2; the title and abstract were also published in English), both hereby expressly incorporated by reference.

BACKGROUND OF THE INVENTION

1. Technical Field of the Invention

The present invention relates to the administration of compositions containing at least one compound selected from among molecules of retinoid type for preventively or curatively treating bacterial colonizations, aggravations of pathologies or disease states caused by these colonizations and also cutaneous overinfections induced by these bacteria and, more particularly, by the bacterium *Staphylococcus aureus*.

The present invention also relates to the formulation of at least one compound selected from among molecules of retinoid type into skin cleansing compositions and also to a cosmetic regime, regimen or treatment for cleansing the skin or correcting its odor, comprising topically applying such compositions onto the skin.

2. Description of the Prior Art

Compounds of retinoid type are compounds with a biological activity profile similar to that of all-trans-retinoic acid or 9-cis-retinoic acid. These compounds can modify the expression of genes by means of receptors of the retinoic acid family, such as the RARs and RXRS. Thus, retinoids may exhibit activity in the test of differentiation of mouse embryonic teratocarcinoma cells (F9) (*Cancer Research*, 43, p. 5268, 1983) and/or in the test of inhibition of ornithine decarboxylase after induction with TPA in mice (*Cancer Research*, 38, p. 793–801, 1978). These tests show the activities of these compounds in the fields of cell differentiation and cell proliferation, respectively.

Such retinoids have already been described as suited for many pharmaceutical applications, more particularly dermatological or cosmetic applications. In the pharmaceutical field, they have especially been proposed to treat dermatological, rheumatic, respiratory, cardiovascular and ophthalmological complaints, conditions or afflictions. In the dermatological or cosmetic field, EP-0,379,367, especially, discloses a method for preventively or curatively treating aged skin with retinoids.

Moreover, it is well known that the skin is covered with a flora that is responsible for an entire range of unpleasant effects ranging from the simple production of odor to more or less severe pathologies such as, for example, acne and/or dandruff.

Commensal microorganisms living on or in the skin may form part of a microflora that is either resident (normal) or transient. The resident organisms develop normally on or in the skin. Their presence is established in well-defined distribution profiles. The microorganisms that are temporarily present are referred to as transient. These microorganisms do not usually become permanently attached; they are incapable of multiplying and normally die after a few hours.

The anatomy and physiology of the skin vary from one part of the body to another and the resident microflora reflect these variations.

Most of the skin bacteria are present on the superficial squamous epidermis, colonizing the dead cells or closely associated with the sebaceous and sweat glands. Excretions from these glands provide water, amino acids, urea, electrolytes and specific fatty acids that serve as nutrient elements principally for *Staphylococcus epidermidis* and aerobic corynebacteria.

Gram-negative bacteria are generally present in the more humid regions. Certain pathogenic agents present on or in the skin are resident/transient and colonize the areas around orifices. *Staphylococcus aureus* is the best example. It is resident in the nostrils and the perianal region, but transient on the other parts of the body, where it has difficulty in surviving.

Theoretically, the epidermis is an unfavorable environment for colonization by microorganisms. Several factors, for instance periodic drying of the skin, the slightly acidic pH of the skin, the high concentration of sodium chloride in the sweat, and certain natural inhibitory substances (bactericides and/or bacteriostatic agents), are responsible for this hostile microenvironment.

The acidic pH (4–6) of the skin, due to the organic acids produced by the staphylococci and to the secretions from the sebaceous and sweat glands, discourages colonization by many microorganisms.

Sweat contains sodium chloride in a concentration that establishes hyperosmotic conditions at the surface of the skin and is an osmotic burden on many microorganisms.

Finally, certain natural inhibitory substances assist in controlling colonization, excessive growth and infection of the surface of the skin by the resident microorganisms. For example, the sweat glands excrete lysozyme which lyses *Staphylococcus epidermidis* and other gram-positive bacteria.

Certain gram-positive bacteria (*Propionibacterium acnes*) can change the lipids secreted by the sebaceous glands into unsaturated fatty acids, such as, for example, oleic acid, which exhibit strong antimicrobial activity on gram-negative bacteria and mycetes.

However, under certain conditions, this natural defense system can, although being effective, elicit unpleasant effects, or may even be neutralized.

For example, certain natural inhibitory substances (bactericides and/or bacteriostatic agents) due to the partial degradation of complex lipids secreted by the sweat glands are volatile and may be associated with a strong odor that it is customary to combat. Admittedly, many deodorants contain antibacterial substances that act selectively on the gram-positive bacteria responsible for these degradations to reduce the production of aromatic unsaturated fatty acids and body odor. However, the deodorants can modify the microflora, essentially in respect of the gram-negative bacteria, and consequently trigger infections.

Need continues to exist, therefore, in the context of treating body odor, for thus effective compounds and/or compositions that present no adverse side effects.

Another example is *Propionibacterium acnes*, the bacterium most commonly associated with the cutaneous glands, which is an anaerobic and lipophilic gram-positive rod. This bacterium is usually harmless. However, it has been associated with a skin disease: juvenile acne. Acne ordinarily appears during adolescence when the endocrine system is very active. The hormonal activity stimulates the overproduction of sebum, a fluid secreted by the sebaceous glands. A large volume of sebum accumulates in the glands and provides a microenvironment that is ideal for *Propionibacterium acnes*. In certain individuals, this accumulation triggers an inflammatory response causing redness and swelling of the glandular duct and producing a comedone, which is a plug of sebum and keratin in the canal. This results in inflammatory lesions (papules, pustules and nodules), commonly known as "blackheads". *Propionibacterium acnes* appears to be the organism that produces lipases which degrade the triglycerides of the sebum into free fatty acids. These derivatives are particularly irritant since they can penetrate into the dermis and promote inflammation.

Strains of *Staphylococcus aureus* are known to produce toxins and superantigens, which promote the appearance of irritation reactions and of inflammatory processes. Thus, more than 90% of cases of atopic dermatitis present this bacterium (*British Journal of Dermatology*, 1998: 139: 13–16).

Moreover, it has been demonstrated that patients suffering from atopic dermatitis can act as reservoirs for the transmission of *Staphylococcus aureus* to other individuals. The studies presented in *Pediatric Dermatology*, Vol. 15, No. 3, 194–198, 1998 suggest that the nostrils and the hands are, respectively, major reservoirs and vectors for transmission of this bacterium to damaged skin and individuals in close contact with these patients.

It is thus important to treat these individuals suffering from atopic dermatitis, in order to prevent the aggravation of the pathology from which they are suffering, and in particular to prevent the risk of massive overinfection with *Staphylococcus aureus*, as is the case for "scalded skin syndrome", but also to take preventive measures with regard to individuals who come into contact with these patients and who are liable to develop bacterial infections, in particular in a hospital environment (*International Journal of Dermatology*, November 1986, Vol. 25, No. 9).

An article published at pages 520 to 532 of the review entitled *The New England Journal of Medicine*, Vol. 339, No. 8 reflects the current state of knowledge regarding the bacterium *Staphylococcus aureus*, its epidemiology and the treatment of diseases in which this bacterium is involved. It will be seen from this article that the levels of colonization are thought to be higher among patients suffering from type 1 diabetes, intravenous-route drug users, blood dialysis patients, patients who have undergone surgery and patients exhibiting the human immunodeficiency syndrome. Individuals with qualitative or quantitative leukocyte defects are also thought to form part of an at-risk population with regard to colonization by the bacterium *Staphylococcus aureus*.

Obviously, it has long been known to treat such afflictions, if necessary, with compounds such as antibiotics.

However, in this case also, it is known that administration of such compounds presents appreciable negative aspects. The abusive use of antibiotics may result in the emergence of resistant microorganisms on which they are no longer effective. Thus, also in this instance, need exists for effective compounds and/or compositions.

In this regard, FR-2,736,548 describes the use of a retinoid for the formulation of a bacterial medicinal product. However, the retinoids administered are aldehydes with weak antibacterial activity and which are, on account of their aldehyde function, cytotoxic and potentially allergizing.

SUMMARY OF THE INVENTION

It has now surprisingly and unexpectedly been found that certain judiciously selected compounds of retinoid type have pronounced antibacterial activity and, in particular, pronounced antibacterial activity towards the bacterium *Staphylococcus aureus*.

DETAILED DESCRIPTION OF BEST MODE AND SPECIFIC/PREFERRED EMBODIMENTS OF THE INVENTION

More particularly, the present invention thus features formulation of at least one compound of retinoid type, in an effective amount, into compositions for preventively or curatively treating bacterial colonizations infecting/infesting mammalian subjects, said at least one retinoid compound being selected from among those compounds 1 to 45 set forth in Table I below:

TABLE I

| NO. | CHEMICAL NAME |
|---|---|
| 1 | 6-[3-(1-Adamantyl)-4-methoxy-5-hydroxyphenyl]-2-naphthoic acid |
| 2 | 4-[4-(6-Methoxymethoxy-4'-methylbiphenyl-2-yl)but-3-en-1-ynyl]benzoic acid |
| 3 | 4-[4-(6-Methoxy-4'-methylbiphenyl-2-yl)but-3-en-1-ynyl]benzoic acid |
| 4 | 6-[2-Methyl-4-hydroxy-5-(1-adamantyl)phenyl]-2-naphthoic acid |
| 5 | 4-[3-(3,5-Di-tert-butyl-4-oxocyclohexa-2,5-dienylidene)prop-1-ynyl]benzoic acid |
| 6 | 2-Hydroxy-4-[4-(4'-methylbiphenyl-2-yl)but-3-en-1-ynyl]benzoic acid |
| 7 | 2-[3-(1-Adamantyl)-4-methoxyphenyl)ethynyl]-4-thiophenecarboxylic acid |
| 8 | 4-[4-(4,4'-Dimethylbiphenyl-2-yl)but-3-en-1-ynyl]benzoic acid |
| 9 | 4-Hydroxy-2'(5,5,8,8-tetramethyl-5,6,7,8-tetrahydronaphthalen-2-yl) [1,1',4',1"]terphenyl-4"-carboxylic acid |
| 10 | 2"-Hydroxy-2'-(5,5,8,8-tetramethyl-5,6,7,8-tetrahydronaphthalen-2-yl) [1,1',4',1"]terphenyl-4"-carboxylic acid |
| 11 | 6-(3-Adamantan-1-yl-5-bromo-4-hydroxyphenyl)-naphthalene-2-carboxylic acid |
| 12 | 4-[4-(6,4'-Dimethylbiphenyl-2-yl)but-3-en-1-ynyl]benzoic acid |
| 13 | 2'-(4,4-Dimethylthiochroman-6-yl) [1,1',4',1"]terphenyl-4"-carboxylic acid |
| 14 | 2'-(3-Hydroxy-5,5,8,8-tetramethyl-5,6,7,8-tetrahydronaphthalen-2-yl) [1,1',4',1"]terphenyl-4"-carboxylic acid |
| 15 | 4-(5,5,8,8-Tetramethyl-5,6,7,8-tetrahydronaphtho-[2,3-b]thiophen-2-yl)benzoic acid |
| 16 | 4-[(6-Hydroxy-7-(1-adamantyl)-2-naphthyl]benzoic acid |
| 17 | 4-[2-Nonyloxyimino-2-(5,5,8,8-tetramethyl-5,6,7,8-tetrahydronaphthalen-2-yl)acetylamino]benzoic acid |
| 18 | 4-[3-Adamantan-1-yl-4-(2-methoxyethoxymethoxy)-phenylethynyl]-2-hydroxybenzoic acid |
| 19 | 4-[[3-(1-Adamantyl)-4-[(2-methyl-3-hydroxypropyloxy)phenyl]ethynyl]]benzoic acid |
| 20 | 2-Hydroxymethyl-5-(5,5,8,8-tetramethyl-5,6,7,8-tetrahydroanthracen-2-yl)phenol |
| 21 | 4-[4-(4'-Propylbiphenyl-2-yl)but-3-en-1-ynyl]benzoic acid |
| 22 | 2-Hydroxy-4-(3,5,5,8,8-pentamethyl-5,6,7,8-tetrahydronaphthalen-2-ylselanylethynyl)benzoic acid |
| 23 | 2'-(3-Methoxy-5,5,8,8-tetramethyl-5,6,7,8-tetrahydronaphthalen-2-yl) [1,1',4',1"]terphenyl-4"-carboxylic acid |
| 24 | 6-[Butoxy-(5,5,8,8-tetramethyl-5,6,7,8-tetrahydronaphthalen-2-yl)methyl]naphthalene-2-carboxylic acid |
| 25 | 4-[3-(1,1-Dimethyldecyl)-4-methoxybenzoylamino]-benzoic acid |
| 26 | 4-(3-Adamantan-1-yl-4-hexyloxybenzoylamino)benzoic acid |
| 27 | 6-[3-(1-Adamantyl)-4-hydroxyphenyl]-2-napthylmethanol |
| 28 | 2-Hydroxy-4-(5,5,8,8-tetramethyl-5,6,7,8-tetrahydroanthracen-2-yl)benzoic acid |
| 29 | 2-(3-Adamantan-1-yl-4-hydroxyphenyl)benzofuran-5-carboxylic acid |
| 30 | 4-[6-Methoxyethoxymethoxy-7-(1-adamantyl)-2-naphthyl]salicylic acid |
| 31 | (E)-4-[4-(5-Methoxymethoxy-4'-methylbiphenyl-2-yl)but-3-en-1-ynyl]benzoic acid |

TABLE I-continued

| NO. | CHEMICAL NAME |
|---|---|
| 32 | 4-[4-(3-Methoxy-4'-methylbiphenyl-2-yl)but-3-en-1-ynyl]benzoic acid |
| 33 | 4-(3,5,5,8,8-Pentamethyl-5,6,7,8-tetrahydronaphthalen-2-ylselanylethynyl)benzoic acid |
| 34 | 2-Methoxymethoxy-2'-(5,5,8,8-tetramethyl-5,6,7,8-tetrahydronaphthalen-2-yl) [1,1',4'1"]terphenyl-4"carboxylic acid |
| 35 | 2-Hydroxy-2'-(5,5,8,8-tetramethyl-5,6,7,8-tetrahydronaphthalen-2-yl) [1,1',4'1"]terphenyl-4"carboxylic acid |
| 36 | 4-[(Z)-2-(5,6,7,8-tetrahydro-5,5,8,8-tetramethyl-2-naphthyl)-2-undecenamido]benzoic acid |
| 37 | 4-[4-(4'-Methylbiphenyl-2-yl)but-3-en-1-ynyl]benzoic acid |
| 38 | 2'-Propoxy-5'-(5,5,8,8-tetramethyl-5,6,7,8-tetrahydronaphthalen-2-yl)bipheny-1-4-carboxylic acid |
| 39 | 4-[2-Heptyloxyimino-2-(5,5,8,8-tetramethyl-5,6,7,8-tetrahydronaphthalen-2-yl)acetylamino]-benzoic acid |
| 40 | 6-(5,5,8,8-Tetramethyl-5,6,7,8-tetrahydronaphthalen-2-yloxy)naphthalene-2-carboxylic acid amide |
| 41 | (2-Dimethylaminoethyl)amide of 6-(3-adamantan-1-yl-4-methoxyphenyl)naphthalene-2-carboxylic acid |
| 42 | 2-Hydroxy-4-(5,5,8,8-tetramethyl-5,6,7,8-tetrahydronaphthalen-2-ylselanylethynyl)benzoic acid |
| 43 | 2'-(3-Methoxymethoxy-5,5,8,8-tetramethyl-5,6,7,8-tetrahydronaphthalen-2-yl) [1,1',4',1"]terphenyl-4"-carboxylic acid |
| 44 | 3-Hydroxy-2'-(5,5,8,8-tetramethyl-5,6,7,8-tetrahydronaphthalen-2-yl) [1,1',4',1"]terphenyl-4"-carboxylic acid |
| 45 | 3-(5'-Adamantan-1-yl-4'-methoxy-2'-methylbiphenyl-3-yl)acrylic acid |

The bacterial colonization that are particularly targeted by the present invention are colonizations by the bacterium *Staphylococcus aureus* and colonizations by the bacterium *Propionibacterium acnes*.

The present invention also features the formulation, in an effective amount, of at least one compound selected from among the compounds 1 to 45 of Table I into compositions for preventively or curatively treating aggravations of pathologies disease states and/or afflictions caused by a bacterial colonization.

Among the pathologies that may be aggravated by a colonization by the bacterium *Staphylococcus aureus*, exemplary are impetigo or atopic dermatitis.

Among the pathologies that may be aggravated by a colonization by the bacterium *Propionibacterium acnes*, exemplary is acne.

Certain compounds indicated in Table I and thus having pronounced antibacterial activity also exhibit biological activity of RAR receptor antagonist type. This is the case, in particular, for the compounds indicated in the list below:

4-[4-(6-Methoxymethoxy-4'-methylbiphenyl-2-yl)but-3-en-1-ynyl]benzoic acid;

4-[4-(6-Methoxy-4'-methylbiphenyl-2-yl)but-3-en-1-ynyl]benzoic acid;

4-(6-Methoxyethoxymethoxy-7-(1-adamantyl)-2-naphthyl]salicylic acid;

(E)-4-[4-(5-Methoxymethoxy-4'-methylbiphenyl-2-yl)but-3-en-1-ynyl]benzoic acid;

4-[4-(3-Methoxy-4'-methylbiphenyl-2-yl)but-3-en-1-ynyl]benzoic acid;

2-Methoxymethoxy-2'-(5,5,8,8-tetramethyl-5,6,7,8-tetrahydronaphthalen-2-yl)[1,1',4'1"]terphenyl-4"-carboxylic acid;

4-[4-(4'-Methylbiphenyl-2-yl)but-3-en-1-ynyl]benzoic acid; and 4-(4-(4'-Propylbiphenyl-2-yl)but-3-en-1-ynyl]benzoic acid.

It too is known that RAR receptor antagonist compounds induce anti-inflammatory and immunomodulatory effects. Thus, in an animal model of chronic eczema, RAR receptor antagonist compounds have elicited inhibitory effects on the clinical and histological signs of inflamation similar to those induced with glucocorticoids or immunomodulators of the macrolide family, for example tacrolimus, without, however, causing the appearance of a side effect such as cutaneous atrophy, as is the case after treatment with glucocorticoids (A. Jomard et al., *J. Invest. Dermatol.* Vol. 110, No, 4, April 1998, page 577).

Thus, the compounds that exhibit pronounced antibacterial activity on *Staphylococcus aureus* and RAR antagonist activity, as is the case for the compounds indicated above, are particularly suitable for treating atopic dermatitis since they act simultaneously on two targets that are anomalies of the immune system and the proliferation of the bacterium *Staphylococcus aureus*.

Other compounds reported in Table I and thus exhibiting pronounced antibacterial activity also have biological activity of RAR receptor agonist type. This is the case, in particular, for the compounds indicated in the list below:

6-[3-(1-Adamantyl)-4-methoxy-5-hydroxyphenyl]-2-naphthoic acid;

4-[3-(3,5-Di-tert-butyl-4-oxocyclohexa-2,5-dienylidene)prop-1-ynyl]benzoic acid;

2-[3-(1-Adamantyl)-4-methoxyphenyl)ethynyl]-4-thiophenecarboxylic acid;

4-Hydroxy-2'(5,5,8,8-tetramethyl-5,6,7,8-tetrahydronaphthalen-2-yl)[1,1',4',1"]terphenyl-4"-carboxylic acid;

2"-Hydroxy-2'-(5,5,8,8-tetramethyl-5,6,7,8-tetrahydronaphthalen-2-yl)[1,1',4',1"]terphenyl-4"-carboxylic acid;

6-(3-Adamantan-1-yl-5-bromo-4-hydroxyphenyl)-naphthalene-2-carboxylic acid;

2'-(4,4-Dimethylthiochroman-6-yl)[1,1',4',1"]terphenyl-4"-carboxylic acid;

2'-(3-Hydroxy-5,5,8,8-tetramethyl-5,6,7,8-tetrahydronaphthalen-2-yl)[1,1',4',1"]terphenyl-4"-carboxylic acid;

4-(5,5,8,8-Tetramethyl-5,6,7,8-tetrahydronaphtho-[2,3-b]thiophen-2-yl)benzoic acid; and 4-[(6-Hydroxy-7-(1-adamantyl)-2-naphthyl]benzoic acid.

And it is known also that RAR receptor agonist compounds modify the differentiation of keratinocytes (keratolytic effects) and of sebocytes (regression of the size of the sebaceous gland) and, by this means, can prevent the formation of comedones, which at least partly explains their beneficial effect in the treatment of acne.

Thus, the compounds that exhibit pronounced antibacterial activity and RAR agonist activity, as is the case for the compounds indicated above, are particularly suitable for treating acne since they act simultaneously on two targets that are anomalies of differentiation of eukaryotic cells (keratinocytes and sebocytes) which is the cause of the formation of comedones and the proliferation of the bacterium *Propionibacterium acnes*.

The present invention also features the formulation, in an effective amount, of at least one compound selected from among the compounds 1 to 45 of Table I into compositions for preventively or curatively treating cutaneous overinfections induced by a bacterial colonization.

Among the cutaneous overinfections induced by a bacterial colonization by the bacterium *Staphylococcus aureus*, exemplary is "scalded skin syndrome".

The pronounced antibacterial activity of the compounds of the present invention on the bacterium *Staphylococcus aureus* may be demonstrated by tests such as those described in the publication entitled "National committee for clinical laboratory standards" Vol. 13, No. 25, December 1993, "Methods for dilution antimicrobial susceptibility tests for bacteria that grow aerobically-third edition, approved standard". The bacterium *Staphylococcus aureus* CIP52.1 may be used in order to determine for each test compound the minimum inhibitory concentration for the bacterium, or MIC, expressed in $\mu$M.

In the present invention, by the expression "compound with pronounced antibacterial activity on the bacterium *Staphylococcus aureus*", is intended any compound that shows in the antibacterial activity test indicated above a minimum inhibitory concentration for the bacterium of less than or equal to 5 $\mu$M. Preferably, the compound with pronounced antibacterial activity on the bacterium *Staphylococcus aureus* has a minimum inhibitory concentration for the bacterium of less than or equal to 2.5 $\mu$M and advantageously less than or equal to 2 $\mu$M.

The test results of the compounds according to the invention are set forth in Example 1 to follow.

The compounds according to the invention may be administered enterally, parenterally, topically or ocularly, for such period of time as required to elicit their desired effect.

Via the enteral route, the pharmaceutical compositions may be formulated as tablets, gel capsules, coated tablets, syrups, suspensions, solutions, powders, granules, emulsions, microspheres, nanospheres or lipid or polymer vesicles providing controlled release. Via the parenteral route, the compositions may be formulated as solutions or suspensions for infusion or for injection.

The compounds according to the invention are generally administered at a daily dose of about from 0.001 mg/kg to 500 mg/kg and preferably of about from 0.01 mg/kg to 50 mg/kg of body weight in 1 to 3 doses.

Via the topical route, the pharmaceutical compositions based on compounds according to the invention are suited for treating the skin and mucous membranes and are typically formulated as ointments, creams, milks, salves, powders, impregnated pads, solutions, gels, sprays, lotions or suspensions. They may also be formulated as lipid or polymer microspheres or nanospheres or vesicles or polymer patches and hydrogels providing controlled release. These topically-applicable compositions may be in anhydrous form, in aqueous form, or in the form of emulsions.

Via the ocular route, they are principally eye drops.

The compounds of the invention are present in these compositions administered via the topical or ocular route at a concentration generally ranging from 0.001% to 10% by weight and preferably from 0.01% to 1% by weight relative to the total weight of the composition.

Preferably, the administration of the compounds or of the compositions according to the invention is by topical application.

The compounds according to the invention are also suitable for cosmetic applications, in particular for body and hair hygiene and more particularly for cleansing the skin or correcting its odor.

The present invention thus features, in particular, in an effective amount, of at least one compound selected from among the compounds 1 to 45 in a composition as an agent for correcting the odor of the skin, or in or for the formulation of a skin cleansing composition.

The present invention also features a cosmetic regime or regimen for cleansing the skin or correcting its odor, by topically applying onto the skin a composition comprising a thus-effective amount of at least one compound selected from among compounds 1 to 45.

The compositions employed in such cosmetic treatment contain, in a physiologically acceptable support (medium, vehicle, diluent or carrier), at least one compound selected from among the compounds 1 to 45 and may especially be formulated as a cream, a milk, a lotion, a gel, lipid or polymer microspheres or nanospheres or vesicles, a soap or a shampoo.

The concentration of the compound selected from among the compounds 1 to 45 in the cosmetic compositions advantageously ranges from 0.001% to 3% by weight.

The compositions according to the invention may, of course, also contain inert or even pharmacodynamically or cosmetically active additives/agents or combinations of these additives/agents and, especially: wetting agents; depigmenting agents such as hydroquinone, azelaic acid, caffeic acid or kojic acid; emollients; moisturizers, for example glycerol, PEG 400, thiamorpholinone and derivatives thereof or urea; antiseborrhic or antiacne agents, such as S-carboxymethylcysteine, S-benzylcysteamine, their salts and derivatives thereof, or benzoyl peroxide; antibiotics, for example erythromycin and esters thereof, neomycin, clindamycin and esters thereof, and tetracyclines; antifungal agents such as ketoconazole or polymethylene-4,5-isothiazolin-3-ones; agents for promoting the regrowth of hair, for example Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenylimidazolidine-2,4-dione); nonsteroidal anti-inflammatory agents; carotenoids and especially $\beta$-carotene; antipsoriatic agents such as anthralin and derivatives thereof, and finally eicosa-5,8,11, 14-tetraynoic acid and eicosa-5,8,11-triynoic acid, their esters and amides or retinoids; D vitamins or derivatives thereof, corticosteroids, free-radical scavengers, $\alpha$-hydroxy or $\alpha$-keto acids or derivatives thereof, or, alternatively, ion-channel blockers.

The subject compositions may also contain agents for improving the taste, preservatives such as para-hydroxybenzoic acid esters, stabilizers, moisture regulators, pH regulators, osmotic pressure modifiers, emulsifiers, UV-A and UV-B screening agents, antioxidants such as $\alpha$-tocopherol, butylhydroxyanisole or butylhydroxytoluene.

One skilled in this art will of course take care to select the optional compound(s) to be incorporated into the subject compositions such that the advantageous properties intrinsically associated with the present invention are not, or are not substantially, adversely affected by the envisaged addition.

In order to further illustrate the present invention and the advantages thereof, the following specific examples are given, it being understood that same are intended only as illustrative and in nowise limitative.

In said examples to follow, several report test results of the antibacterial activity of the compounds according to the invention and include comparative examples on the bacterium *Staphylococcus aureus*. Also included are various specific formulations according to the invention.

Also in said examples to follow, all parts and percentages are given by weight unless otherwise indicated.

EXAMPLE 1

This example illustrates various results of biological tests that evidence the antibacterial properties of the compounds of the invention on the bacterium *Staphylococcus aureus*.

The technique employed to determine the minimum inhibitory concentration or MIC was that described in the publication entitled "National committee for clinical laboratory standards" Vol. 13, No. 25, December 1993; Methods for dilution antimicrobial susceptibility tests for bacteria that grow aerobically-third edition, approved standard". This minimum inhibitory concentration gives an indication as to the bacteriostatic effect of the test compounds, i.e., the capacity of these compounds to stop the proliferation of the bacterium.

Each compound of the invention was tested at least three times. The average of the test results was calculated, along with the standard deviation. The reference compound used was gentamycin. The results obtained are reported in the following Table II:

TABLE II

MIC RESULTS (µM) - TABLE II

| COMPOUND | MEAN | STANDARD DEVIATION |
|---|---|---|
| GENTAMYCIN | 0.11 | 0.06 |
| 1 | 1.04 | 0.36 |
| 2 | 1.04 | 0.36 |
| 3 | 1.04 | 0.36 |
| 4 | 1.25 | 0.00 |
| 5 | 1.25 | 0.00 |
| 6 | 1.25 | 0.00 |
| 7 | 1.66 | 0.72 |
| 8 | 1.66 | 0.72 |
| 9 | 1.66 | 0.72 |
| 10 | 1.66 | 0.72 |
| 11 | 2.08 | 0.72 |
| 12 | 2.08 | 0.72 |
| 13 | 2.08 | 0.72 |
| 14 | 2.08 | 0.72 |
| 15 | 2.50 | 0.00 |
| 16 | 2.50 | 0.00 |
| 17 | 2.50 | 0.00 |
| 18 | 2.50 | 0.00 |
| 19 | 2.50 | 0.00 |
| 20 | 2.50 | 0.00 |
| 21 | 2.50 | 0.00 |
| 22 | 2.50 | 0.00 |
| 23 | 2.50 | 0.00 |
| 24 | 3.33 | 1.44 |
| 25 | 3.33 | 1.44 |
| 26 | 3.33 | 1.44 |
| 27 | 3.33 | 1.44 |
| 28 | 3.33 | 1.44 |
| 29 | 3.33 | 1.44 |
| 30 | 3.33 | 1.44 |
| 31 | 3.33 | 1.44 |
| 32 | 3.33 | 1.44 |
| 33 | 3.33 | 1.44 |
| 34 | 3.33 | 1.44 |
| 35 | 3.33 | 1.44 |
| 36 | 4.16 | 1.44 |
| 37 | 4.16 | 1.44 |
| 38 | 4.16 | 1.44 |
| 39 | 5.00 | 0.00 |
| 40 | 5.00 | 0.00 |
| 41 | 5.00 | 4.33 |
| 42 | 5.00 | 0.00 |
| 43 | 5.00 | 4.33 |
| 44 | 5.00 | 0.00 |
| 45 | 5.00 | 0.00 |

These results evidence the antibacterial activity of the compounds the invention on the bacterium *Staphylococcus aureus*.

EXAMPLE 2

This example illustrates various results of biological tests that evidence the superiority of the antibacterial properties of the compounds of the invention on the bacterium *Staphylococcus aureus* compared with retinaldehyde compounds which are described in the French patent application of Pierre Fabre, No. FR-2,736,548.

The technique employed to determine the MIC values was the same as that described in Example 1.

The technique employed to determine the minimum bactericidal concentration, or MBC, was that described in *Bactéricidie*, P. Courvalin et al., Editions Maloine, 1990, chapter 7, page 335.

This minimum bactericidal concentration provides an indication as to the bactericidal effect of the test compounds, i.e., the capacity of these compounds to kill the bacterium.

Each compound of the invention and each comparative example taken from the Pierre Fabre patent application No. FR-2,736,548 was tested at least three times. The mean of the test results was calculated, along with the standard deviation. The reference compound used was gentamycin. The results obtained are reported in the following Tables III and IV:

Comparative Example 1 was all-trans-retinaldehyde.
Comparative Example 2 was 9-cis-retinaldehyde.
Comparative Example 3 was 13-cis-retinaldehyde.

TABLE III

MIC RESULTS (µM)

| COMPOUND | MEAN | STANDARD DEVIATION |
|---|---|---|
| Gentamycin | 0.14 | 0.06 |
| Compound 1 | 1.30 | 0.45 |
| Compound 5 | 3.30 | 2.57 |
| Compound 2 | 2.45 | 1.37 |
| Comparative Example 1 | 11.64 | 5.85 |
| Comparative Example 2 | 11.52 | 5.95 |
| Comparative Example 3 | 7.64 | 2.40 |

These results evidence that the compounds of the invention show better bacteriostatic activities on the bacterium *Staphylococcus aureus* than the compounds of the prior art.

TABLE IV

MIC RESULTS (µM)

| | MEAN | STANDARD DEVIATION |
|---|---|---|
| Gentamycin | 0.26 | 0.05 |
| Compound 1 | 12.50 | 0.00 |
| Compound 5 | 13.18 | 7.30 |
| Compound 2 | 16.65 | 8.33 |
| Comparative Example 1 | 26.33 | 13.39 |
| Comparative Example 2 | 16.63 | 4.15 |
| Comparative Example 3 | 15.97 | 7.89 |

These results evidence that the compounds of the invention show bactericidal activities on the bacterium *Staphylococcus aureus* that are equivalent to those of the compounds of the prior art.

Thus, these results evidence that the compounds of the invention are equally as bactericidal on the bacterium *Staphylococcus aureus*, but are much more bacteriostatic than the compounds of the prior art, which indicates that the compounds of the invention have overall better antibacterial activities on the bacterium *Staphylococcus aureus* than the compounds of the prior art.

EXAMPLE 3

This example illustrates various specific formulations based on the compounds according to the invention.

A. ORAL ROUTE:

(a) 0.2 g Tablet:

| | |
|---|---|
| Compound 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules:

| | | |
|---|---|---|
| Compound 5 | | 0.001 g |
| Glycerol | | 0.500 g |
| 70% sorbitol | | 0.500 g |
| Sodium saccharinate | | 0.010 g |
| Methyl para-hydroxybenzoate | | 0.040 g |
| Flavoring | | qs |
| Purified water | qs | 5 ml |

(c) 0.8 g Tablet:

| | |
|---|---|
| Compound 2 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampules:

| | | |
|---|---|---|
| Compound 4 | | 0.200 g |
| Glycerol | | 1.000 g |
| 70% sorbitol | | 1.000 g |
| Sodium saccharinate | | 0.010 g |
| Methyl para-hydroxybenzoate | | 0.080 g |
| Flavoring | | qs |
| Purified water | qs | 10 ml |

B. TOPICAL ROUTE:

(a) Ointment:

| | |
|---|---|
| Compound 1 | 0.020 g |
| Isopropyl myristate | 81.700 g |
| Fluid liquid paraffin | 9.100 g |
| Silica ("Aerosil 200" marketed by Degussa) | 9.180 g |

(b) Ointment:

| | | |
|---|---|---|
| Compound 2 | | 0.300 g |
| White petroleum jelly codex | qs | 100 g |

(c) Nonionic water-in-oil cream:

| | | |
|---|---|---|
| Compound 1 | | 0.100 g |
| Mixture of emulsifying lanolin alcohols, waxes and oils ("Anhydrous eucerin" marketed by BDF) | | 39.900 g |
| Methyl para-hydroxybenzoate | | 0.075 g |
| Propyl para-hydroxybenzoate | | 0.075 g |
| Sterile demineralized water | qs | 100 g |

(d) Lotion:

| | |
|---|---|
| Compound 3 | 0.100 g |
| Polyethylene glycol (PEG 400) | 69.900 g |
| 95% ethanol | 30.000 g |

(e) Hydrophobic ointment:

| | | |
|---|---|---|
| Compound 5 | | 0.300 g |
| Isopropyl myristate | | 36.400 g |
| Silicone oil ("Rhodorsil 47 V 300" marketed by Rhodia) | | 36.400 g |
| Beeswax | | 13.600 g |
| Silicone oil ("Abil 300 000 cst" marketed by Goldschmidt) | qs | 100 g |

B. TOPICAL ROUTE:

(f) Nonionic oil-in-water cream:

| | | |
|---|---|---|
| Compound 2 | | 1.000 g |
| Cetyl alcohol | | 4.000 g |
| Glyceryl monostearate | | 2.500 g |
| PFG-50 stearate | | 2.500 g |
| Karite butter | | 9.200 g |
| Propylene glycol | | 2.000 g |
| Methyl para-hydroxybenzoate | | 0.075 g |
| Propyl para-hydroxybenzoate | | 0.075 g |
| Sterile demineralized water | qs | 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for killing bacteria or hindering the proliferation of bacteria, said method comprising administering to an individual subject infested or infected with a colonization of bacteria, a bactericidally or bacteriostatically effective amount of at least one retinoid compound selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

6-[2-methyl-4-hydroxy-5-(1-adamantyl)phenyl]-2-naphthoic acid;

4-[3-(3,5-di-tert-butyl-4-oxocyclohexa-2,5-dienylidene)prop-1-ynyl]benzoic acid;

2-hydroxy-4-[4-(4'-methylbiphenyl-2-yl)but-3-en-1-ynyl]benzoic acid;

2-[3-(1-adamantyl)-4-methoxyphenyl)ethynyl]-4-thiophenecarboxylic acid;

4-[4-(4,4'-dimethylbiphenyl-2-yl)but-3-en-1-ynyl]benzoic acid;

4-hydroxy-2'-(5,5,8,8-tetramethyl-5,6,7,8-tetrahydronaphthalen-2-yl)-[1,1';4',1"]terphenyl-4"-carboxylic acid;

2"-hydroxy-2'-(5,5,8,8-tetramethyl-5,6,7,8-tetrahydronaphthalen-2-yl)-(1,1';4',1"]terphenyl-4"-carboxylic acid;

6-(3-adamantan-1-yl-5-bromo-4-hydroxyphenyl)naphthalene-2-carboxylic acid;

4-[4-(6,4'-dimethylbiphenyl-2-yl)but-3-en-1-ynyl]benzoic acid;

2'-(4,4-dimethylthiochroman-6-yl)-[1,1';4',1"]terphenyl-4"-carboxylic acid;

2'-(3-hydroxy-5,5,8,8-tetramethyl-5,6,7,8-tetrahydronaphthalen-2-yl)-[1,1';4',1"]terphenyl-4"-carboxylic acid;

4-(5,5,8,8-tetramethyl-5,6,7,8-tetrahydronaphtho[2,3-b]thiophen-2-yl)benzoic acid;

4-[(6-hydroxy-7-(1-adamantyl)-2-naphthyl]benzoic acid;

4-(2-nonyloxyimino-2-(5,5,8,8-tetramethyl-5,6,7,8-tetrahydronaphthalen-2-yl)acetylamino]benzoic acid;

4-[3-adamantan-1-yl-4-(2-methoxyethoxymethoxy)phenylethynyl)-2-hydroxybenzoic acid;

4-[[3-(1-adamantyl)-4-[(2-methyl-3-hydroxypropyloxy)phenyl]ethynyl]]benzoic acid;

2-hydroxymethyl-5-(5,5,8,8-tetramethyl-5,6,7,8-tetrahydroanthracen-2-yl)phenol;

4-[4-(4'-propylbiphenyl-2-yl)but-3-en-1-ynyl]benzoic acid;

2-hydroxy-4-(3,5,5,8,8-pentamethyl-5,6,7,8-tetrahydronaphthalen-2-ylselanylethynyl)benzoic acid;

2'-(3-methoxy-5,5,8,8-tetramethyl-5,6,7,8-tetrahydronaphthalen-2-yl)-[1,1';4',1"]terphenyl-4"-carboxylic acid;

6-[butoxy-(5,5,8,8-tetramethyl-5,6,7,8-tetrahydronaphthalen-2-yl)methyl]naphthalene-2-carboxylic acid;

4-[3-(1,1-dimethyldecyl)-4-methoxybenzoylamino]benzoic acid;

4-(3-adamantan-1-yl-4-hexyloxybenzoylamino)benzoic acid;

6-[3-(1-adamantyl)-4-hydroxyphenyl]-2-naphthylmethanol;

2-hydroxy-4-(5,5,8,8-tetramethyl-5,6,7,8-tetrahydroanthracen-2-yl)benzoic acid;

2-(3-adamantan-1-yl-4-hydroxyphenyl)benzofuran-5-carboxylic acid;

4-(6-methoxyethoxymethoxy-7-(1-adamantyl)-2-naphthyl]salicylic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid;

4-(3,5,5,8,8-pentamethyl-5,6,7,8-tetrahydronaphthalen-2-ylselanylethynyl)benzoic acid;

2-methoxymethoxy-2'-(5,5,8,8-tetramethyl-5,6,7,8-tetrahydronaphthalen-2-yl)-[1,1';4',1"]terphenyl-4"-carboxylic acid;

2-hydroxy-2'-(5,5,8,8-tetramethyl-5,6,7,8-tetrahydronaphthalen-2-yl)-[1,1';4',1"]terphenyl-4"-carboxylic acid;

4-[(Z)-2-(5,6,7,8-tetrahydro-5,5,8,8-tetramethyl-2-naphthyl)-2-undecenamido]benzoic acid;

4-[4-(4'-methylbiphenyl-2-yl)but-3-en-1-ynyl]benzoic acid;

2'-propoxy-5'-(5,5,8,8-tetramethyl-5,6,7,8-tetrahydronaphthalen-2-yl)biphenyl-4-carboxylic acid;

4-[2-heptyloxyimino-2-(5,5,8,8-tetramethyl-5,6,7,8-tetrahydronaphthalen-2-yl)acetylamino]benzoic acid;

6-(5,5,8,8-tetramethyl-5,6,7,8-tetrahydronaphthalen-2-yloxy)naphthalene-2-carboxylic acid amide;

(2-dimethylaminoethyl)amide of 6-(3-adamantan-1-yl-4-methoxyphenyl)naphthalene-2-carboxylic acid;

2-hydroxy-4-(5,5,8,8-tetramethyl-5,6,7,8-tetrahydronaphthalen-2-ylselanylethynyl)benzoic acid;

2'-(3-methoxymethoxy-5,5,8,8-tetramethyl-5,6,7,8-tetrahydronaphthalen-2-yl)-[1,1';4',1"]terphenyl-4"-carboxylic acid;

3-hydroxy-2'-(5,5,8,8-tetramethyl-5,6,7,8-tetrahydronaphthalen-2-yl)-[1,1';4',1"]terphenyl-4"-carboxylic acid; and 3-(5'-adamantan-1-yl-4'-methoxy-2'-methylbiphenyl-3-yl)acrylic acid.

2. The method according to claim 1, wherein said at least one retinoid compound is selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

6-[2-methyl-4-hydroxy-5-(1-adamantyl)phenyl]-2-naphthoic acid;

4-[3-(3,5-di-tert-butyl-4-oxocyclohexa-2,5-dienylidene)prop-1-ynyl]benzoic acid;

2-hydroxy-4-[4-(4'-methylbiphenyl-2-yl)but-3-en-1-ynyl]benzoic acid;

4-[4-(4,4'-dimethylbiphenyl-2-yl)but-3-en-1-ynyl]benzoic acid;

6-(3-adamantan-1-yl-5-bromo-4-hydroxyphenyl)naphthalene-2-carboxylic acid;

4-[4-(6,4'-dimethylbiphenyl-2-yl)but-3-en-1-ynyl]benzoic acid;

4-[4-(4'-propylbiphenyl-2-yl)but-3-en-1-ynyl]benzoic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid; and

4-[4-(4'-methylbiphenyl-2-yl)but-3-en-1-ynyl]benzoic acid.

3. The method according to claim 2 wherein said at least one retinoid compound is selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid; and

4-[3-(3,5-di-tert-butyl-4-oxocyclohexa-2,5-dienylidene)prop-1-ynyl]benzoic acid.

4. The method as defined by claim 1, wherein said individual subject suffers from a pathological disease state, condition or affliction aggravated by the bacterial colonization.

5. The method as defined by claim 2, wherein said individual subject suffers from a pathological disease state, condition or affliction aggravated by the bacterial colonization.

6. The method as defined by claim 3, wherein said individual subject suffers from a pathological disease state, condition or affliction aggravated by the bacterial colonization.

7. The method as defined by claim 1, wherein said individual subject suffers from a cutaneous overinfection induced by the bacterial colonization.

8. The method as defined by claim 2, wherein said individual subject suffers from a cutaneous overinfection induced by the bacterial colonization.

9. The method as defined by claim 3, wherein said individual subject suffers from a cutaneous overinfection induced by the bacterial colonization.

10. A method for killing bacteria or hindering the proliferation of bacteria on the skin of an individual human subject, said human subject being afflicted with an objectionable colonization of bacteria on the skin, and for thus cleansing said skin, said method comprising topically applying to said skin a bactericidally or bacteriostatically effective amount of at least one retinoid compound selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

6-[2-methyl-4-hydroxy-5-(1-adamantyl)phenyl]-2-naphthoic acid;

4-[3-(3,5-di-tert-butyl-4-oxocyclohexa-2,5-dienylidene)prop-1-ynyl]benzoic acid;

2-hydroxy-4-[4-(4'-methylbiphenyl-2-yl)but-3-en-1-ynyl]benzoic acid;

2-[3-(1-adamantyl)-4-methoxyphenyl)ethynyl]-4-thiophenecarboxylic acid;

4-[4-(4,4'-dimethylbiphenyl-2-yl)but-3-en-1-ynyl]benzoic acid;

4-hydroxy -2'-(5,5,8,8-tetramethyl-5,6,7,8-tetrahydronaphthalen-2-yl)-[1,1';4',1"]terphenyl-4"-carboxylic acid;

2"-hydroxy-2'-(5,5,8,8-tetramethyl-5,6,7,8-tetrahydronaphthalen-2-yl)-(1,1';4',1"]terphenyl-4"-carboxylic acid;

6-(3-adamantan-1-yl-5-bromo-4-hydroxyphenyl)naphthalene-2-carboxylic acid,

4-[4-(6,4'-dimethylbiphenyl-2-yl)but-3-en-1-ynyl]benzoic acid;

2'-(4,4-dimethylthiochroman-6-yl)-[1,1';4',1"]terphenyl-4"-carboxylic acid;

2'-(3-hydroxy-5,5,8,8-tetramethyl-5,6,7,8-tetrahydronaphthalen-2-yl)-[1,1';4',1"]terphenyl-4"-carboxylic acid;

4-(5,5,8,8-tetramethyl-5,6,7,8-tetrahydronaphtho[2,3-b]thiophen-2-yl)benzoic acid;

4-[(6-hydroxy-7-(1-adamantyl)-2-naphthyl]benzoic acid;

4-(2-nonyloxyimino-2-(5,5,8,8-tetramethyl-5,6,7,8-tetrahydronaphthalen-2-yl)acetylamino]benzoic acid;

4-[3-adamantan-1-yl-4-(2-methoxyethoxymethoxy)phenylethynyl)-2-hydroxybenzoic acid;

4-[[3-(1-adamantyl)-4-[(2-methyl-3-hydroxypropyloxy)phenyl]ethynyl]]benzoic acid;

2-hydroxymethyl-5-(5,5,8,8-tetramethyl-5,6,7,8-tetrahydroanthracen-2-yl)phenol;

4-[4-(4'-propylbiphenyl-2-yl)but-3-en-1-ynyl]benzoic acid;

2-hydroxy-4-(3,5,5,8,8-pentamethyl-5,6,7,8-tetrahydronaphthalen-2-ylselanylethynyl)benzoic acid;

2'-(3-methoxy-5,5,8,8-tetramethyl-5,6,7,8-tetrahydronaphthalen-2-yl)-[1,1';4',1"]terphenyl-4"-carboxylic acid;

6-[butoxy-(5,5,8,8-tetramethyl-5,6,7,8-tetrahydronaphthalen-2-yl)methyl]naphthalene-2-carboxylic acid;

4-[3-(1,1-dimethyldecyl)-4-methoxybenzoylamino]benzoic acid;

4-(3-adamantan-1-yl-4-hexyloxybenzoylamino)benzoic acid;

6-[3-(1-adamantyl)-4-hydroxyphenyl]-2-naphthylmethanol;

2-hydroxy-4-(5,5,8,8-tetramethyl-5,6,7,8-tetrahydroanthracen-2-yl)benzoic acid;

2-(3-adamantan-1-yl-4-hydroxyphenyl)benzofuran-5-carboxylic acid;

4-(6-methoxyethoxymethoxy-7-(1-adamantyl)-2-naphthyl]salicylic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid;

4-(3,5,5,8,8-pentamethyl-5,6,7,8-tetrahydronaphthalen-2-ylselanylethynyl)benzoic acid;

2-methoxymethoxy-2'-(5,5,8,8-tetramethyl-5,6,7,8-tetrahydronaphthalen-2-yl)-[1,1';4',1"]terphenyl-4"-carboxylic acid;

2-hydroxy-2'-(5,5,8,8-tetramethyl-5,6,7,8-tetrahydronaphthalen-2-yl)-[1,1';4',1"]terphenyl-4"-carboxylic acid;

4-[(Z)-2-(5,6,7,8-tetrahydro-5,5,8,8-tetramethyl-2-naphthyl)-2-undecenamido]benzoic acid;

4-[4-(4'-methylbiphenyl-2-yl)but-3-en-1-ynyl]benzoic acid;

2'-propoxy-5'-(5,5,8,8-tetramethyl-5,6,7,8-tetrahydronaphthalen-2-yl)biphenyl-4-carboxylic acid;

4-[2-heptyloxyimino-2-(5,5,8,8-tetramethyl-5,6,7,8-tetrahydronaphthalen-2-yl)acetylamino]benzoic acid;

6-(5,5,8,8-tetramethyl-5,6,7,8-tetrahydronaphthalen-2-yloxy)naphthalene-2-carboxylic acid amide;

(2-dimethylaminoethyl)amide of 6-(3-adamantan-1-yl-4-methoxyphenyl)naphthalene-2-carboxylic acid;

2-hydroxy-4-(5,5,8,8-tetramethyl-5,6,7,8-tetrahydronaphthalen-2-ylselanylethynyl)benzoic acid;

2'-(3-methoxymethoxy-5,5,8,8-tetramethyl-5,6,7,8-tetrahydronaphthalen-2-yl)-[1,1';4',1"]terphenyl-4"-carboxylic acid;

3-hydroxy-2'-(5,5,8,8-tetramethyl-5,6,7,8-tetrahydronaphthalen-2-yl)-[1,1';4',1"]terphenyl-4"-carboxylic acid; and 3-(5'-adamantan-1-yl-4'-methoxy-2'-methylbiphenyl-3-yl)acrylic acid.

11. The method as defined by claim 10, wherein said at least one retinoid compound is selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

6-[2-methyl-4-hydroxy-5-(1-adamantyl)phenyl]-2-naphthoic acid;

4-[3-(3,5-di-tert-butyl-4-oxocyclohexa-2,5-dienylidene)prop-1-ynyl]benzoic acid;

2-hydroxy-4-[4-(4'-methylbiphenyl-2-yl)but-3-en-1-ynyl]benzoic acid;

4-[4-(4,4'-dimethylbiphenyl-2-yl)but-3-en-1-ynyl]benzoic acid;

6-(3-adamantan-1-yl-5-bromo-4-hydroxyphenyl)naphthalene-2-carboxylic acid;

4-[4-(6,4'-dimethylbiphenyl-2-yl)but-3-en-1-ynyl]benzoic acid;

4-[4-(4'-propylbiphenyl-2-yl)but-3-en-1-ynyl]benzoic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid; and

4-[4-(4'-methylbiphenyl-2-yl)but-3-en-1-ynyl]benzoic acid.

12. The method as defined by claim 10, wherein said at least one retinoid compound is selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid; and

4-[3-(3,5-di-tert-butyl-4-oxocyclohexa-2,5-dienylidene)prop-1-ynyl]benzoic acid.

13. A method for deodorizing or correcting the odor of the skin of an individual human subject afflicted with a malodorous bacterial colonization on said skin, said method comprising topically applying to said skin a bactericidally or bacteriostatically effective amount of at least one retinoid compound selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

6-[2-methyl-4-hydroxy-5-(1-adamantyl)phenyl]-2-naphthoic acid;

4-[3-(3,5-di-tert-butyl-4-oxocyclohexa-2,5-dienylidene)prop-1-ynyl]benzoic acid;

2-hydroxy-4-[4-(4'-methylbiphenyl-2-yl)but-3-en-1-ynyl]benzoic acid;

2-[3-(1-adamantyl)-4-methoxyphenyl)ethynyl]-4-thiophenecarboxylic acid;

4-[4-(4,4'-dimethylbiphenyl-2-yl)but-3-en-1-ynyl]benzoic acid;

4-hydroxy-2'-(5,5,8,8-tetramethyl-5,6,7,8-tetrahydronaphthalen-2-yl)-[1,1';4',1"]terphenyl-4"-carboxylic acid;

2"-hydroxy-2'-(5,5,8,8-tetramethyl-5,6,7,8-tetrahydronaphthalen-2-yl)-(1,1';4',1"]terphenyl-4"-carboxylic acid;

6-(3-adamantan-1-yl-5-bromo-4-hydroxyphenyl)naphthalene-2-carboxylic acid;

4-[4-(6,4'-dimethylbiphenyl-2-yl)but-3-en-1-ynyl]benzoic acid;

2'-(4,4-dimethylthiochroman-6-yl)-[1,1';4',1"]terphenyl-4"-carboxylic acid;

2'-(3-hydroxy-5,5,8,8-tetramethyl-5,6,7,8-tetrahydronaphthalen-2-yl)-[1,1';4',1"]terphenyl-4"-carboxylic acid;

4-(5,5,8,8-tetramethyl-5,6,7,8-tetrahydronaphtho[2,3-b]thiophen-2-yl)benzoic acid;

4-[(6-hydroxy-7-(1-adamantyl)-2-naphthyl]benzoic acid;

4-(2-nonyloxyimino-2-(5,5,8,8-tetramethyl-5,6,7,8-tetrahydronaphthalen-2-yl)acetylamino]benzoic acid;

4-[3-adamantan-1-yl-4-(2-methoxyethoxymethoxy)phenylethynyl)-2-hydroxybenzoic acid;

4-[[3-(1-adamantyl)-4-[(2-methyl-3-hydroxypropyloxy)phenyl]ethynyl]]benzoic acid;

2-hydroxymethyl-5-(5,5,8,8-tetramethyl-5,6,7,8-tetrahydroanthracen-2-yl)phenol;

4-[4-(4'-propylbiphenyl-2-yl)but-3-en-1-ynyl]benzoic acid;

2-hydroxy-4-(3,5,5,8,8-pentamethyl-5,6,7,8-tetrahydronaphthalen-2-ylselanylethynyl)benzoic acid;

2'-(3-methoxy-5,5,8,8-tetramethyl-5,6,7,8-tetrahydronaphthalen-2-yl)-[1,1';4',1"]terphenyl-4"-carboxylic acid;

6-[butoxy-(5,5,8,8-tetramethyl-5,6,7,8-tetrahydronaphthalen-2-yl)methyl]naphthalene-2-carboxylic acid;

4-[3-(1,1-dimethyldecyl)-4-methoxybenzoylamino]benzoic acid;

4-(3-adamantan-1-yl-4-hexyloxybenzoylamino)benzoic acid;

6-[3-(1-adamantyl)-4-hydroxyphenyl]-2-naphthylmethanol;

2-hydroxy-4-(5,5,8,8-tetramethyl-5,6,7,8-tetrahydroanthracen-2-yl)benzoic acid;

2-(3-adamantan-1-yl-4-hydroxyphenyl)benzofuran-5-carboxylic acid;

4-(6-methoxyethoxymethoxy-7-(1-adamantyl)-2-naphthyl]salicylic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid;

4-(3,5,5,8,8-pentamethyl-5,6,7,8-tetrahydronaphthalen-2-ylselanylethynyl)benzoic acid;

2-methoxymethoxy-2'-(5,5,8,8-tetramethyl-5,6,7,8-tetrahydronaphthalen-2-yl)-[1,1';4',1"]terphenyl-4"-carboxylic acid;

2-hydroxy-2'-(5,5,8,8-tetramethyl-5,6,7,8-tetrahydronaphthalen-2-yl)-[1,1';4',1"]terphenyl-4"-carboxylic acid;

4-[(Z)-2-(5,6,7,8-tetrahydro-5,5,8,8-tetramethyl-2-naphthyl)-2-undecenamido]benzoic acid;

4-[4-(4'-methylbiphenyl-2-yl)but-3-en-1-ynyl]benzoic acid;

2'-propoxy-5'-(5,5,8,8-tetramethyl-5,6,7,8-tetrahydronaphthalen-2-yl)biphenyl-4-carboxylic acid;

4-[2-heptyloxyimino-2-(5,5,8,8-tetramethyl-5,6,7,8-tetrahydronaphthalen-2-yl)acetylamino]benzoic acid;

6-(5,5,8,8-tetramethyl-5,6,7,8-tetrahydronaphthalen-2-yloxy)naphthalene-2-carboxylic acid amide;

(2-dimethylaminoethyl)amide of 6-(3-adamantan-1-yl-4-methoxyphenyl)naphthalene-2-carboxylic acid;

2-hydroxy-4-(5,5,8,8-tetramethyl-5,6,7,8-tetrahydronaphthalen-2-ylselanylethynyl)benzoic acid;

2'-(3-methoxymethoxy-5,5,8,8-tetramethyl-5,6,7,8-tetrahydronaphthalen-2-yl)-[1,1';4',1"]terphenyl-4"-carboxylic acid;

3-hydroxy-2'-(5,5,8,8-tetramethyl-5,6,7,8-tetrahydronaphthalen-2-yl)-[1,1';4',1"]terphenyl-4"-carboxylic acid; and 3-(5'-adamantan-1-yl-4'-methoxy-2'-methylbiphenyl-3-yl)acrylic acid.

14. The method as defined by claim 13, wherein said at least one retinoid compound is selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

6-[2-methyl-4-hydroxy-5-(1-adamantyl)phenyl]-2-naphthoic acid;

4-[3-(3,5-di-tert-butyl-4-oxocyclohexa-2,5-dienylidene)prop-1-ynyl]benzoic acid;

2-hydroxy-4-[4-(4'-methylbiphenyl-2-yl)but-3-en-1-ynyl]benzoic acid;

4-[4-(4,4'-dimethylbiphenyl-2-yl)but-3-en-1-ynyl]benzoic acid;

6-(3-adamantan-1-yl-5-bromo-4-hydroxyphenyl)naphthalene-2-carboxylic acid;

4-[4-(6,4'-dimethylbiphenyl-2-yl)but-3-en-1-ynyl]benzoic acid;

4-[4-(4'-propylbiphenyl-2-yl)but-3-en-1-ynyl]benzoic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid; and

4-[4-(4'-methylbiphenyl-2-yl)but-3-en-1-ynyl]benzoic acid.

15. The method as defined by claim 14, wherein said at least one retinoid compound is selected from the group consisting of:

6-[3-(1-adamantyl)-4-methoxy-5-hydroxyphenyl]-2-naphthoic acid;

4-[4-(6-methoxymethoxy-4'-methylbiphenyl-2-yl)but-3-en-1-ynyl]benzoic acid; and

4-[3-(3,5-di-tert-butyl-4-oxocyclohexa-2,5-dienylidene)prop-1-ynyl]benzoic acid.

16. The method as defined by claim 1, wherein the bacterium responsible for the bacterial colonization is *Staphylococcus aureus*.

17. The method as defined by claim 2, wherein the bacterium responsible for the bacterial colonization is *Staphylococcus aureus*.

18. The method as defined by claim 3, wherein the bacterium responsible for the bacterial colonization is *Staphylococcus aureus*.

19. The method as defined by claim 10, wherein the bacterium responsible for the bacterial colonization is *Staphylococcus aureus*.

20. The method as defined by claim 11, wherein the bacterium responsible for the bacterial colonization is *Staphylococcus aureus*.

21. The method as defined by claim 12, wherein the bacterium responsible for the bacterial colonization is *Staphylococcus aureus*.

22. The method as defined by claim 13, wherein the bacterium responsible for the bacterial colonization is *Staphylococcus aureus*.

23. The method as defined by claim 14, wherein the bacterium responsible for the bacterial colonization is *Staphylococcus aureus*.

24. The method as defined by claim 15, wherein the bacterium responsible for the bacterial colonization is *Staphylococcus aureus*.

25. The method as defined by claim 1, wherein the bacterium responsible for the bacterial colonization is *Propionibacterium acnes*.

26. The method as defined by claim 2, wherein the bacterium responsible for the bacterial colonization is *Propionibacterium acnes*.

27. The method as defined by claim 3, wherein the bacterium responsible for the bacterial colonization is *Propionibacterium acnes*.

28. The method as defined by claim 10, wherein the bacterium responsible for the bacterial colonization is *Propionibacterium acnes*.

29. The method as defined by claim 11, wherein the bacterium responsible for the bacterial colonization is *Propionibacterium acnes*.

30. The method as defined by claim 12, wherein the bacterium responsible for the bacterial colonization is *Propionibacterium acnes*.

31. The method as defined by claim 13, wherein the bacterium responsible for the bacterial colonization is *Propionibacterium acnes*.

32. The method as defined by claim 14, wherein the bacterium responsible for the bacterial colonization is *Propionibacterium acnes*.

33. The method as defined by claim 15, wherein the bacterium responsible for the bacterial colonization is *Propionibacterium acnes*.

34. The method as defined by claim 7, wherein said cutaneous overinfection is scalded skin syndrome.

35. The method as defined by claim 8, wherein said cutaneous overinfection is scalded skin syndrome.

36. The method as defined by claim 9, wherein said cutaneous overinfection is scalded skin syndrome.

37. The method as defined by claim 4, wherein said pathological disease state, condition or affliction is impetigo.

38. The method as defined by claim 5, wherein said pathological disease state, condition or affliction is impetigo.

39. The method as defined by claim 6, wherein said pathological disease state, condition or affliction is impetigo.

40. The method as defined by claim 4, wherein said pathological disease state, condition or affliction is atopic dermatitis.

41. The method as defined by claim 5, wherein said pathological disease state, condition or affliction is atopic dermatitis.

42. The method as defined by claim 6, wherein said pathological disease state, condition or affliction is atopic dermatitis.

43. The method as defined by claim 40, wherein said at least one retinoid compound is selected from the group consisting of:

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

4-[6-methoxyethoxymethoxy-7-(1-adamantyl)-2-naphthyl]salicylic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid;

2-methoxymethoxy-2'-(5,5,8,8-tetramethyl-5,6,7,8-tetrahydronaphthalen-2-yl)-[1,1';4',1"]terphenyl-4"-carboxylic acid;

4-[4-(4'-methylbiphenyl-2-yl)but-3-en-1-ynyl]benzoic acid; and

4-[4-(4'-propylbiphenyl-2-yl)but-3-en-1-ynyl]benzoic acid.

44. The method as defined by claim 43, wherein said at least one retinoid compound is selected from the group consisting of:

4-[4-(6-methoxymethoxy-4'-methylbiphenyl-2-yl)but-3-en-1-ynyl]benzoic acid;

4-[4-(6-methoxy-4'-methylbiphenyl-2-yl)but-3-en-1-ynyl]benzoic acid;

(E)-4-[4-(5-methoxymethoxy-4'-methylbiphenyl-2-yl)but-3-en-1-ynyl]benzoic acid;

4-[4-(3-methoxy-4'-methylbiphenyl-2-yl)but-3-en-1-ynyl]benzoic acid;

4-[4-(4'-methylbiphenyl-2-yl)but-3-en-1-ynyl]benzoic acid; and

4-[4-(4'-propylbiphenyl-2-yl)but-3-en-1-ynyl]benzoic acid.

45. The method as defined by claim 43, wherein said at least one retinoid compound is 4-[4-(6-methoxymethoxy-4'-methylbiphenyl-2-yl)but-3-en-1-ynyl]benzoic acid.

46. The method as defined by claim 4, wherein said pathological disease state, condition or affliction is acne.

47. The method as defined by claim 5, wherein said pathological disease state, condition or affliction is acne.

48. The method as defined by claim 6, wherein said pathological disease state, condition or affliction is acne.

49. The method as described by claim 46, wherein said at least one retinoid compound is selected from the group consisting of:

6-[3-(1-adamantyl)-4-methoxy-5-hydroxyphenyl]-2-naphthoic acid;

4-[3-(3,5-di-tert-butyl-4-oxocyclohexa-2,5-dienylidene)prop-1-ynyl]benzoic acid;

2-[3-(1-adamantyl)-4-methoxyphenyl)ethynyl]-4-thiophenecarboxylic acid;

4-hydroxy-2'-(5,5,8,8-tetramethyl-5,6,7,8-tetrahydronaphthalen-2-yl)-[1,1';4',1"]terphenyl-4"-carboxylic acid;

2"-hydroxy-2'-(5,5,8,8-tetramethyl-5,6,7,8-tetrahydronaphthalen-2-yl)-[1,1';4',1"]terphenyl-4"-carboxylic acid;

6-(3-adamantan-1-yl-5-bromo-4-hydroxyphenyl)naphthalene-2-carboxylic acid;

2'-(4,4-dimethylthiochroman-6-yl)-[1,1';4'1"]terphenyl-4"-carboxylic acid;

2'-(3-hydroxy-5,5,8,8-tetramethyl-5,6,7,8-tetrahydronaphthalen-2-yl)-[1,1';4',1"]terphenyl-4"-carboxylic acid;

4-(5,5,8,8-tetramethyl-5,6,7,8-tetrahydronaphtho[2,3-b]thiophen-2-yl)benzoic acid; and 4-[(6-hydroxy-7-(1-adamantyl)-2-naphthyl]benzoic acid.

50. The method as defined by claim 49, wherein said at least one retinoid compound is selected from the group consisting of:

6-[3-(1-adamantyl)-4-methoxy-5-hydroxyphenyl]-2-naphthoic acid;

4-[3-(3,5-di-tert-butyl-4-oxocyclohexa-2,5-dienylidene)prop-1-ynyl]benzoic acid; and 6-(3-adamantan-1-yl-5-bromo-4-hydroxyphenyl)naphthalene-2-carboxylic acid.

51. The method as defined by claim 49, wherein said at least one retinoid compound is selected from the group consisting of 6-[3-(1-adamantyl-4-methoxy-5-hydroxyphenyl]-2-naphthoic acid and 4-[3-(3,5-di-tert-butyl-4-oxocyclohexa-2,5-dienylidene)prop-1-ynyl]benzoic acid.

52. The method as defined by claim 1, comprising co-administering to said individual subject an effective amount of at least one other retinoid, D vitamin or derivative thereof, corticosteroid, free-radical scavenger, α-hydroxy or α-keto acid or derivative thereof, ion-channel blocker, or combination thereof.

53. The method as defined by claim 1, comprising administering to said individual subject a pharmaceutical composition comprising from 0.001% to 10% by weight of said at least one retinoid compound.

54. The cosmetic method for cleansing human skin as defined by claim 10, comprising topically applying thereon a physiologically acceptable cosmetic composition comprising from 0.001% to 3% by weight of said at least one retinoid compound.

55. The cosmetic method for deodorizing or correcting the odor of human skin as defined by claim 13, comprising topically applying thereon a physiologically acceptable cosmetic composition comprising from 0.001% to 3% by weight of said at least one retinoid compound.

* * * * *